United States Patent [19]

Nishihagi et al.

[11] Patent Number: 5,568,531
[45] Date of Patent: Oct. 22, 1996

[54] SURFACE DEFECT EVALUATING APPARATUS

[75] Inventors: Kazuo Nishihagi, Hirakata; Atsushi Kawabata, Kyoto, both of Japan

[73] Assignee: Technos Co., Ltd., Osaka, Japan

[21] Appl. No.: 428,566

[22] Filed: Apr. 25, 1995

[30] Foreign Application Priority Data

Sep. 27, 1994 [JP] Japan ................................. 6-231781

[51] Int. Cl.⁶ .................................................. G01N 23/70
[52] U.S. Cl. .................................................. 378/71; 378/73
[58] Field of Search ........................ 378/71, 73, 136, 378/138, 87

[56] References Cited

U.S. PATENT DOCUMENTS 5,170,422  12/1992  Fiebiger ................................ 378/136

FOREIGN PATENT DOCUMENTS 6-267693  9/1994  Japan ................................ 378/71

Primary Examiner—David P. Porta
Attorney, Agent, or Firm—Brinks Hofer Gilson & Lione

[57] ABSTRACT

A surface defect evaluating apparatus comprises an X-ray generator having a non-winding type cathode, a first slit device for shaping the X-ray flux from the X-ray generator, a diffraction crystal for obliquely receiving a slit-form X-ray flux passing through the slit device and diffracting the X-ray flux on a specific crystal plane, a second slit device for shaping the X-ray flux from the diffraction crystal, a photographic plate for detecting the intensity distribution of the flux diffracted on the specific crystal plane of a sample such as a semiconductor wafer after a slit-form X-ray flux passing through the second slit device obliquely irradiates the sample, a slit device, and a scintillator, installed at the back side of the photographic plate for detecting the intensity of the X-ray flux.

4 Claims, 3 Drawing Sheets

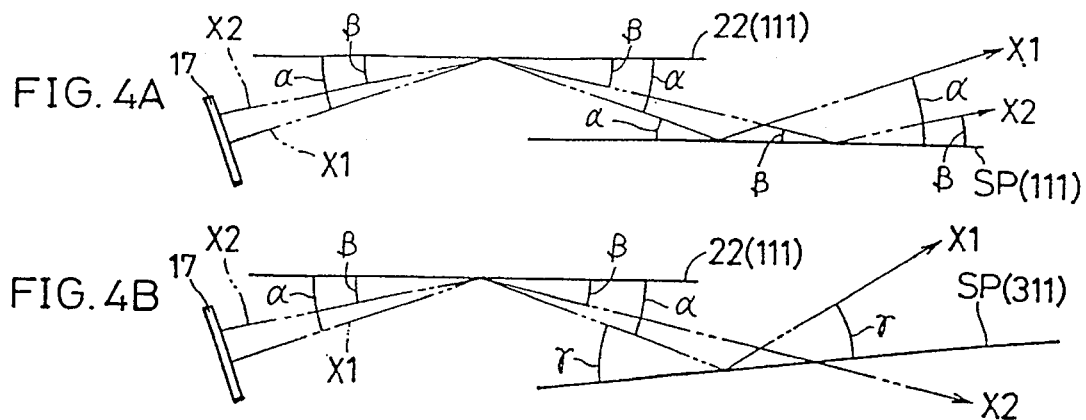
FIG. 5
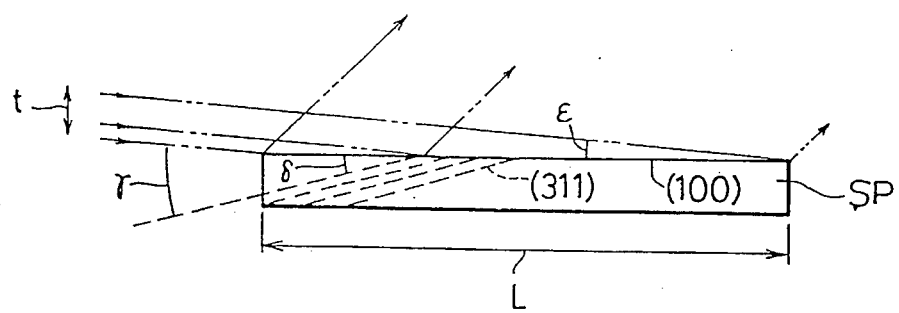
FIG. 6
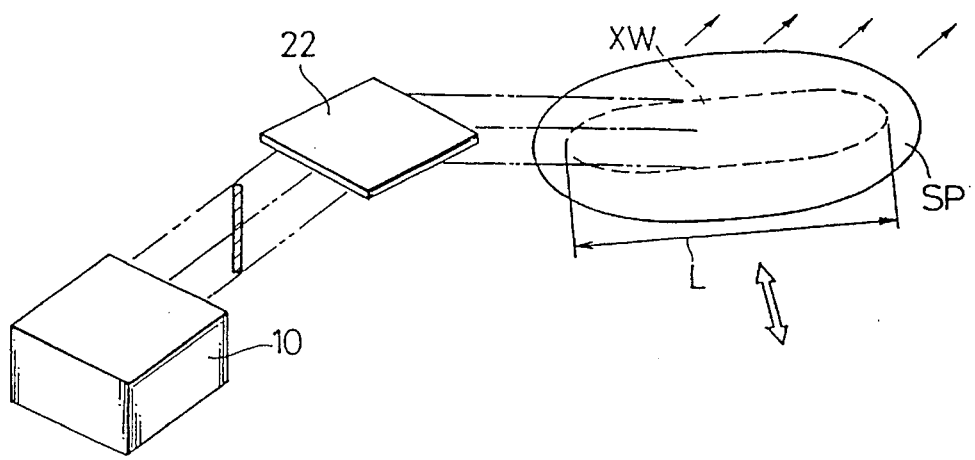

SURFACE DEFECT EVALUATING APPARATUS

BACKGROUND OF THE INVENTION

The present invention relates to a surface defect evaluating apparatus making use of X-ray diffraction topography, wherein X-ray diffraction is utilized to measure the spatial distribution of defects such as lattice defects and lattice distortion contained in a single crystal specimen.

X-ray diffraction topography is capable of observing defects such as dislocation, lamination defects, twinning plane, impurity precipitation and segregation in a single crystal having an excellent quality and a small dislocation density. The resolution of measurement is determined by the size of an X-ray source utilized, the geometric condition of the apparatus, the wavelength width of X-rays, the particle size of a photographic plate, and the like. Various methods have been proposed for X-ray diffraction topography.

According to Lang's method, an X-ray flux is emitted to irradiate a thin sample spot, and the diffracted X-rays passing through the sample are recorded on a photographic plate. By scanning the sample and photographic plate along the crystal plane to be measured, the defect distribution in a wide region of the sample is taken on one photograph.

According to the Berg-Barrett method, the X-ray source is kept away in order to improve the collimation of the X-ray flux through a slit before the X-ray flux enters a sample. Additionally, the photographic plate is placed near the sample surface so that the diffracted X-rays reflected on the surface may enter the photographic plate vertically.

In the double crystal method, the X-ray flux beam is diffracted by a first crystal to improve the collimation before irradiating a second crystal which is the sample to be analyzed, and thereafter the X-rays reflected and diffracted from the sample are recorded on the photographic plate.

In the conventional X-ray diffraction topographic method, however, using a winding-type tungsten filament as the cathode of the X-ray tube, the intensity distribution of electron beams radiated from the cathode is uneven, corresponding to the coarse and dense distribution of filaments. Accordingly, the intensity-distribution of X-rays generated from the anode target is not spatially uniform. Such a non-uniform X-ray flux causes the recording density on the photographic plate to fluctuate spatially, and as a result the measuring precision is greatly impaired.

SUMMARY OF THE INVENTION

It is therefore a primary object of the invention to present a surface defect evaluating apparatus capable of evaluating surface defects of a sample at high spatial resolution and precision in a short time.

To achieve this object, the present invention provides a surface defect evaluating apparatus comprising:

an X-ray generator for generating an X-ray flux, a diffraction crystal for diffracting the X-ray flux from the X-ray generator on a predetermined crystal plane, and an X-ray imager device for detecting the intensity distribution of the X-ray flux diffracted by a predetermined crystal plane in a sample after the X-ray flux diffracted by the diffraction crystal obliquely irradiates the sample surface, wherein the X-ray generator includes an anode and a non-winding type cathode, an electron beam focus is formed in linear shape on the anode, a slit-form X-ray flux is generated along a direction substantially perpendicular to the longitudinal direction of the beam focus, and the longitudinal direction of the X-ray flux is set nearly parallel to an incident plane to the sample. Preferably, the incident angle and the diffraction angle of the X-ray flux with respect to the sample surface are different.

In a preferred embodiment of the invention, the cathode has a thermoelectron generating part composed of $LaB_6$ crystal or $LaB_6$ sinter, and is of a direct-heating type based on Joule-heating of the thermoelectron generating part, or of an indirect-heating type, in which the thermoelectron generating part is sandwiched between heating elements.

The invention further provides a surface defect evaluating apparatus comprising:

an X-ray generator for generating an X-ray flux, a diffraction crystal for diffracting the X-ray flux from the X-ray generator on a predetermined crystal plane, an X-ray imager device for detecting the intensity distribution of the X-ray flux diffracted by a predetermined crystal plane in a sample after the X-ray flux diffracted by the diffraction crystal obliquely irradiates the sample surface, a sample holder for holding the sample and adjusting the posture of the sample, an X-ray detector for detecting the intensity of the X-ray flux diffracted by the sample, and a controller for controlling the sample holder on the basis of the output from the X-ray detector.

According to the invention, by using the non-winding type cathode in the X-ray generator, electron beams having a uniform intensity are emitted from the cathode, and an X-ray flux having a uniform intensity is generated from the line focus on the anode. Hence, error factors of the cathode have no influence on the X-ray information taken by the X-ray imager device, such as a photographic plate. Accordingly, an X-ray topography with a less uneven density is obtained, allowing evaluation at a high precision.

Moreover, a slit-form X-ray flux is generated along an almost-perpendicular direction to the longitudinal direction of the line focus formed on the anode, and the longitudinal direction of the X-ray flux is set nearly parallel to the incident plane to the sample. For example, as compared with the conventional X-ray flux from a point focus having a section of about 1 mm×1 mm, the X-ray flux of the invention realizes an extended section of about 10 mm×0.1 mm, and consequently the X-ray irradiation region of the sample is enlarged, with the result that the area to be taken by one photographing operation is increased up to about 200 mm×30 mm and the entire measuring time can be shortened.

Furthermore, since the X-ray flux is nearly collimated by Bragg reflection on the diffraction crystal, the spatial resolution in the longitudinal direction hardly deteriorates. Further, the width of the X-ray flux is smaller than that of the conventional X-ray flux, greatly improving the spatial resolution in the widthwise direction, thereby achieving a spatial resolution of, for example, about 5 μm.

Additionally, by employing a so-called asymmetric reflection configuration in which the incident angle and the diffraction angle of the X-ray flux with respect to the sample surface are different, it is possible to detect the X-ray diffraction on the crystal plane, positioned obliquely to the sample surface and to use a small incident angle of the X-ray flux, so that the X-ray irradiation region on the sample can be further extended. It is also possible to use a different diffraction interplanar spacing in the diffraction crystal from that of the sample, and as a result the X-ray wavelength which satisfies the diffraction conditions on both the diffraction crystal and the sample is limited. Therefore, even if the X-rays from the X-ray generator are white X-rays or a multispectrum, the X-rays reaching the X-ray imager device are set monochromatic, and a ghost image due to an undesired X-ray wavelength can be avoided.

Further, the cathode of the X-ray generator has a thermoelectron generating part preferably composed of $LaB_6$-crystal or $LaB_6$-sinter, and therefore a non-winding type cathode with an excellent thermoelectron emission efficiency is realized. Additionally, since the cathode is either of a direct heating type, such that Joule-heating of the thermoelectron generating part is conducted, or of an indirect heating type such that the thermoelectron generating part is sandwiched between heating elements, the temperature distribution of the cathode is uniform, and as a result an electron beam with a uniform intensity distribution is realized.

Further, according to the invention it is possible to adjust the orientation of the sample while detecting the intensity of the X-ray flux diffracted by the sample, and for example, by adjusting the orientation of the sample so that the X-ray diffraction intensity on the sample may be maximum, the X-ray intensity reaching the X-ray imager device is enhanced, so that the configuration for optimizing measuring sensitivity can be set easily.

BRIEF DESCRIPTION OF THE DRAWINGS

Other and further objects, features, and advantages of the invention will be apparent from the following detailed description taken with reference to the drawings, wherein:

FIG. 4A shows a configuration of symmetric reflection on the sample SP, and FIG. 4B shows a configuration of asymmetric reflection on the sample SP;

FIG. 5 is a diagram showing an X-ray irradiation region of the sample SP; and

FIG. 6 is a perspective view showing a mode of X-ray diffraction topography.

DETAILED DESCRIPTION OF THE PREFERRED EMBODIMENT

Figure 1:
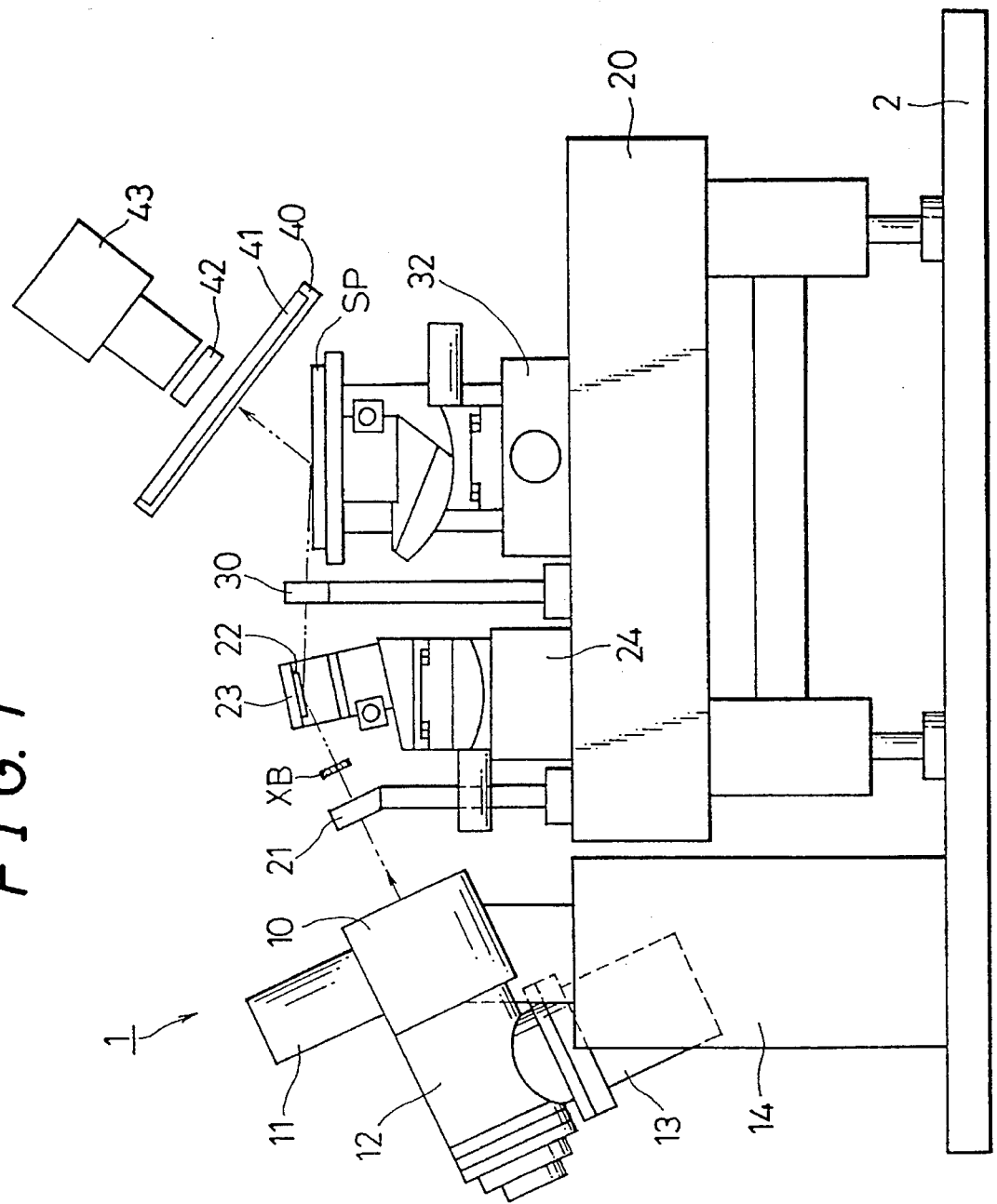
FIG. 1 is a front view showing an embodiment of the invention.

Now referring to the drawings, preferred embodiments of the invention are described below.

FIG. 1 is a front view showing an embodiment of the invention. A surface defect evaluating apparatus 1 comprises an X-ray generator 10 for generating an X-ray flux, a slit device 21 for shaping the X-ray flux from the X-ray generator 10, a diffraction crystal 22 for obliquely receiving a slit-form X-ray flux passing through the slit device 21 and diffracting on a predetermined crystal plane, a slit device 30 for shaping the X-ray flux emitted from the diffraction crystal 22, a photographic plate 41 for detecting the intensity distribution of the X-ray flux diffracted on a predetermined crystal plane in a sample SP, such as a semiconductor wafer, the slit-form X-ray flux passing through the slit device 30 irradiates obliquely the sample SP, a slit device 42 and a scintillator 43 installed on the back side of the photographic plate 41 for detecting the intensity of the X-ray flux.

The X-ray generator 10 generates X-rays peculiar to the anode material, wherein the electron emitted from the cathode collides against the anode. FIG. 1 shows a rotating anode type that includes motor 11 for rotating the anode. A fixed-type X-ray tube having a fixed anode may be also used. The X-ray generator 10 is provided with a high voltage circuit 12 for controlling the voltage applied to the cathode and the anode, and a vacuum pump 13 for creating and maintaining a vacuum environment about the cathode and anode. The X-ray generator 10 is supported on a support stand 14 so as to incline upward to the horizontal plane, and is further fixed on a base 2.

Figure 2A:
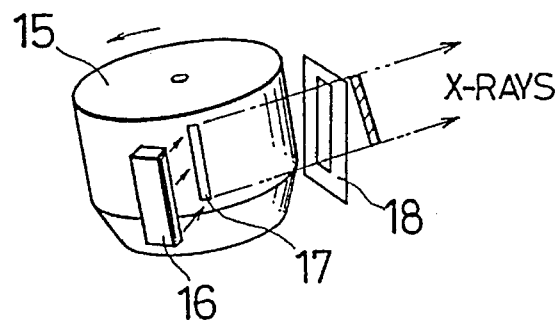
FIG. 2A is a schematic perspective view showing a configuration of an anode 15 and a cathode 16 of an X-ray generator 10.
Figure 2B:
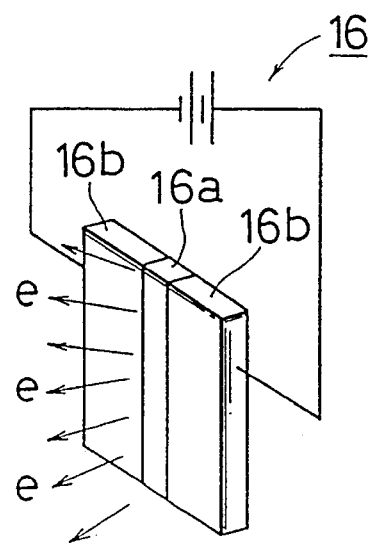
FIG. 2B is a structural diagram of the cathode 16.

FIG. 2A is a schematic perspective view showing a configuration of anode 15 and cathode 16 of the X-ray generator 10, and FIG. 2B is a structural diagram of the cathode 16. The anode 15 may be composed of copper, molybdenum, or the like in a columnar form, and is pivoted so as to rotate at a specific speed. Confronting the side surface of the anode 15, the cathode 16 is disposed so that the rotary shaft of the anode 15 and the longitudinal direction of the cathode 16 may be nearly parallel to each other.

The cathode 16 is of a non-winding type without filament structure, and is an indirect heating type cathode having a thermoelectron generating part 16a made of a slender $LaB_6$ sinter sandwiched between heating elements 16b made of carbon or the like as shown in FIG. 2B. As an electric current flows in the lamination direction, the heating elements 16b, having a high electric resistance are heated, the thermoelectron generating part 16a is raised in temperature, and thermoelectrons are emitted in a slit form. Thus, electron beams with a uniform intensity distribution can be obtained.

Since a high voltage is applied between the cathode 16 and anode 15, as shown in FIG. 2A, electrons emitted from the cathode 16 collide against the anode 15 while nearly retaining the shape of the cathode 16, and form a line focus 17. X-rays are radially generated from the line focus 17, and by picking up through a slit 18 the X-rays generated in the nearly-vertical direction to the longitudinal direction of the line focus and in the tangential direction to the side surface of the anode 15, a slit-form X-ray flux with uniform intensity distribution is obtained.

This explanation refers to an example of the cathode 16 of the indirect heating type using a $LaB_6$ sinter, but the thermoelectron generating part 16a may be formed of $LaB_6$ crystal, or other materials than $LaB_6$ may be also used. Additionally, instead of using the heating elements 16b, the cathode 16 may be of a direct heating type, and applying an electric current directly to the thermoelectron generating part 16a causes the thermoelectron generating part 16a itself to generate Joule heat.

Referring again to FIG. 1, the X-ray flux generated upward from the X-ray generator 10 passes through the slit device 21, and the X-ray flux is collimated and the sectional form is shaped into an appropriate one. The section XB of the X-ray flux obtained at this time is about 10 mm×0.1 mm, and its longitudinal direction is parallel to the sheet of paper.

The X-ray flux passing through the slit device 21 enters obliquely a diffraction crystal 22, and is diffracted on a predetermined crystal plane. The diffraction crystal 22 is made of a single crystal material with extremely small dislocation such as Si and Ge, and its surface is set to be, for example, a (111) crystal plane. The diffraction crystal 22 is fixed in the upper inner surface of a U-shaped holder 23, and the X-ray flux passes through the holder 23. The holder 23 is mounted on a fine adjustment stage 24 having motors mounted on the respective control axes thereof, and the posture and height of the diffraction crystal 22 are adjusted at a high precision by remote control. In the diffraction crystal 22, only the X-ray flux satisfying the Bragg reflection condition determined by the interplanar spacing of a diffraction crystal plane, X-ray wavelength and incident angle is diffracted at a specific angle.

The X-ray flux diffracted by the diffraction crystal 22 passes through the slit device 30 and is collimated, and the sectional form is shaped into an appropriate one. Thereafter the X-ray flux enters the surface of the sample SP at a small angle, and is diffracted on a specific crystal plane of the sample SP. At this time, the longitudinal direction of the X-ray flux is set to be nearly parallel to the incident plane into the sample (parallel to the sheet of paper).

The X-ray flux diffracted on the specific crystal plane of the sample SP directly advances in parallel and exposes the photographic plate 41 detachably mounted on the holder 40. After a specified exposure time, the sample SP and photographic plate 41 are displaced relatively to the X-ray flux to radiograph again with the X-ray flux, and by repeating this step the entire surface of the sample SP can be photographed. Afterwards, through a development process, the intensity distribution of diffracted X-rays is recorded as changes in density.

When the sample SP is a sound crystal with few defects, almost all incident X-ray fluxes satisfy the X-ray diffraction conditions, and the exposure amount to the photographic plate 41 increases, thereby increasing the density. On the other hand, if the sample SP has any defect, the X-ray diffraction conditions are not satisfied in the defect portion of the sample, and the exposure amount to the photographic plate 41 decreases with the result that the density drops. Therefore it is known that a surface defect is present in the portion of the sample SP corresponding to the region where the recording density is low. Similar X-ray topographs can be obtained by using a photosensitive film, a semiconductor area sensor, an imaging plate or the like, in place of the photographic plate 41, as an X-ray imager device.

Figure 3:
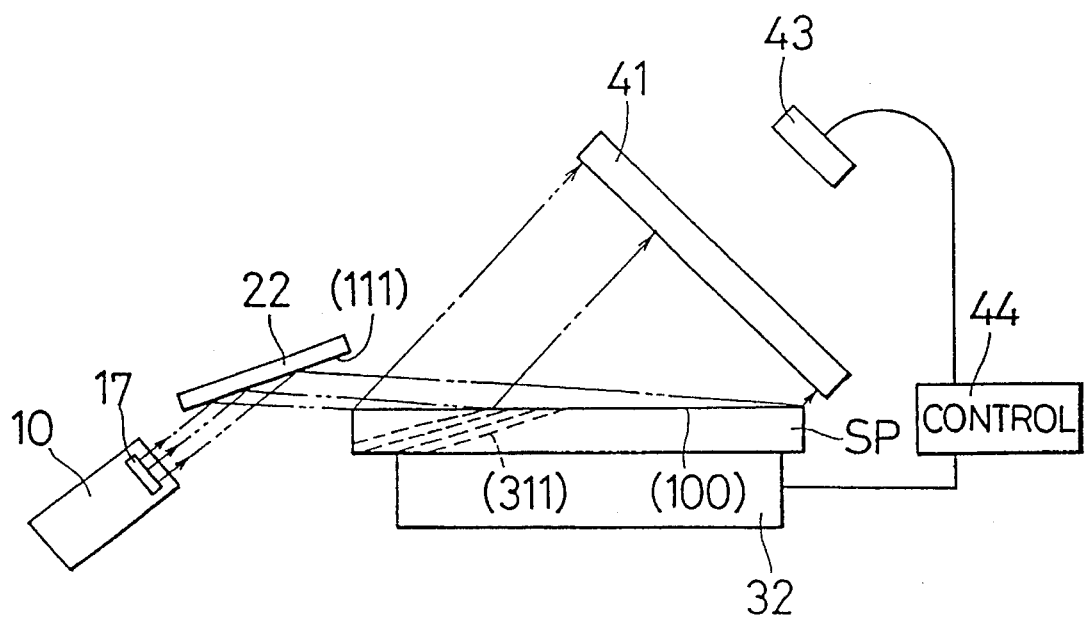
FIG. 3 is a magnified view showing a mode of X-ray diffraction of a sample SP.

FIG. 3 is a magnified view showing a mode of X-ray diffraction of a sample SP. The X-ray flux diffracted on the (111) plane which is the surface of the diffraction crystal 22 enters the sample SP at a low angle so as to irradiate almost all the surface of the sample SP. Incidentally, when using a Si wafer as the sample SP, the cut section of the surface is often the (100) plane. The X-ray flux entering the sample SP satisfies Bragg reflection condition on the (311) crystal plane of the sample SP, and the X-ray incident angle and reflection angle coincide with respect to the (311) plane. On the other hand, since the surface of the sample SP and the (311) plane intersect at a specific angle, the configuration of asymmetric reflection is set up in which the incident angle and diffraction angle of X-ray flux with respect to the surface of the sample SP differ from each other. Meanwhile, the diffraction crystal plane of the sample SP is not limited to the (311) plane, but a crystal plane with other plane indices (Millar indices) may be used. In order to select an arbitrary crystal plane by adjusting the posture of the sample SP, the sample SP is held on a fine adjustment stage 32 having motors mounted on respective control axes. The fine adjustment stage 32 is controlled by a control circuit 44, and is operated while the output signal from a scintillator 43 is monitored. When adjusting the posture and height of the sample SP, the photographic plate 41 is taken out of the holder 40, and the X-ray flux diffracted by the sample SP is intended to directly enter the scintillator 43 installed at the back side of the holder 40, and the fine adjustment stage 32 is controlled so that the output signal from the scintillator 43 may be maximized.

Referring to FIG. 1, the fine adjustment stages 23, 32, slit devices 21, 30, holder 40, scintillator 43 and others are fixed on a vibration-proof table 20 to prevent external vibration from adversely affecting the X-ray exposure. In particular, the table 20 is installed separately from the support stand 14 in order to prevent vibration from the motor 11 which drives the rotating anode.

FIG. 4A shows a configuration of symmetric reflection on the sample SP, and FIG. 4B shows a configuration of asymmetric reflection on the sample SP. From the line focus 17 of the X-ray generator 10, X-rays with different wavelengths are generated, such as Cu-Ka1 (hereinafter called X1) and Cu-Ka2 ray (hereinafter called X2), and are diffracted on the (111) plane of the diffraction crystal 22.

In FIG. 4A, X1 satisfies the diffraction condition of Bragg angle $\alpha$, and X2 satisfies the diffraction condition of Bragg angle $\beta$. Furthermore, the (111) plane of the sample SP has the same interplanar spacing as the (111) plane of the diffraction crystal 22, and they are disposed in parallel to each other. X1 and X2 entering the sample SP similarly satisfy the diffraction conditions of Bragg angles $\alpha$, $\beta$, respectively. Accordingly, since both X1 and X2 reach the photographic plate, and the diffraction angle is deviated depending on the difference in wavelength, a ghost image is formed in the X-ray topography and as a result it becomes hard to observe the X-ray topography.

On the other hand, in FIG. 4B, the diffraction plane of the sample SP is set to be the (311) plane having a different interplanar spacing from the (111) plane of the diffraction crystal 22, and the angle of the diffraction plane of the sample SP is set so that X1 entering the sample SP may satisfy the diffraction condition of Bragg angle $\gamma$. X2, entering the sample SP does not satisfy the Bragg reflection condition on the (311) plane, and hence X2 passes through without being diffracted. Accordingly, only X1 reaches the photographic plate, and an X-ray topography having a high resolution without a ghost image is obtained.

FIG. 5 is a diagram showing the x-ray irradiation region of the sample SP. When a Si wafer for integrated circuit manufacturing is used as the sample SP, the cut face is often the (100) plane, and when a high order inclined crystal plane, such as (311) plane, is used as the X-ray diffraction plane, the angle $\gamma$ formed by the incident direction of X-ray flux and crystal plane is 28.060 degrees, and the angle $\delta$ formed by the (100) surface and (311) plane is 25.239 degrees, and therefore, by subtraction, the incident angle $\epsilon$ amounts to 2.821 degrees. Such a small incident angle $\epsilon$ allows for enlargement of the region that can be analyzed at once, and using the width t of the incident X-ray flux, incident angle $\epsilon$, and length L of the irradiation field, $t = L \times \sin \epsilon$ is established.

For example, to observe at once from end to end a Si wafer having a diameter of 8 inches, putting L=200 mm, $\epsilon$=2.821 degrees yields t=9.84 mm. That is, by using an X-ray generator having a line focus of about 10 mm, surface defects of an 8-inch wafer can be evaluated in a short time.

FIG. 6 is a perspective view showing a mode of X-ray diffraction topography. A slender X-ray flux is generated by the X-ray generator 10, and diffracted by the diffraction crystal 22, and a long region XW having a length L is irradiated on the sample Sp, such as an eight inch wafer. The width of the region XW amounts to about 30 mm, somewhat expanded from the X-ray generator 10, and by exposing the sample SP to X-rays in about seven divided portions while conveying in steps in the direction orthogoval to the region XW, the entire surface of the sample SP can be analyzed on one photographic plate.

Meanwhile, at every step of conveying the sample SP, it may go out of the diffraction condition due to a conveying error, and therefore the optimum posture of the fine adjustment stage 32 is stored in a memory bank in every conveying position by using the scintillator 43 before mounting the photographic plate 41, and the fine adjustment stage 32 is adjusted corresponding to each conveying position after start of topography. Thus, while conveying the sample SP in steps, an optimum position can be set promptly and continuously.

In the conventional method having an x-ray irradiation region of about 20 mm×20 mm, it takes about a whole day to take one wafer, whereas the recording time required can be reduced up to about an hour using the present invention.

In this invention, since high resolution topography is possible, the desired resolution is assured if the X-ray generator 10 and the sample SP are situated close to each other. In the conventional method, the distance between the X-ray source and the sample is required to be about 2 m, whereas it can be shortened to about 60 cm in the present invention, and the X-ray intensity is thus increased. Additionally, the attainable measuring precision is enhanced and the measuring time is shortened.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. A surface defect evaluating apparatus comprising:

an X-ray generator for generating an X-ray flux, a diffraction crystal for diffracting the X-ray flux from the X-ray generator on a predetermined crystal plane, and an X-ray imager device for detecting the intensity distribution of the X-ray flux diffracted by a predetermined crystal plane in a sample after the X-ray flux diffracted by the diffraction crystal obliquely irradiates a surface of the sample, wherein the X-ray generator includes an anode and a non-winding type cathode, an electron beam focus is formed in linear shape on the anode, a slit form X-ray flux is generated along a direction substantially perpendicular to the longitudinal direction of the beam focus, and the longitudinal direction of the X-ray flux is set nearly parallel to a plane including incident X-rays and diffracted X-rays in relation to the sample.

2. The apparatus of claim 1, wherein the incident angle and the diffraction angle of the X-ray flux with respect to the sample surface are different.

3. The apparatus of claim 1, wherein the cathode has a thermoelectron generating part composed of $LaB_6$ crystal or $LaB_6$ sinter, and is of a direct heating type.

4. The apparatus of claim 1, wherein the cathode has a thermoelectron generating part composed of $LaB_6$ crystal or $LaB_6$ sinter, and is of an indirect heating type, said thermoelectron generating part disposed between heating elements.

* * * * *